(12) United States Patent
Von Malottki (10) Patent No.: US 10,182,886 B2
(45) Date of Patent: Jan. 22, 2019

(54) INSERTION POST FOR TRANSFERRING LOCATION AND ORIENTATION OF AT LEAST ONE IMPLANT INTRODUCED IN THE JAW OF A PATIENT ONTO A MODEL, AND ASSOCIATED IMPRESSION POST

(71) Applicant: SIC INVENT AG, Basel (CH)

(72) Inventor: Marcus Von Malottki, Erkrath (DE)

(73) Assignee: SIC INVENT AG, Basel (CH)

( * ) Notice: Subject to any disclaimer, the term of this patent is extended or adjusted under 35 U.S.C. 154(b) by 0 days.

(21) Appl. No.: 14/168,675

(22) Filed: Jan. 30, 2014

(65) Prior Publication Data

US 2014/0227664 A1    Aug. 14, 2014

(30) Foreign Application Priority Data

Jan. 31, 2013 (EP) .................................. 13153477

(51) Int. Cl.
*A61C 8/00* (2006.01)
(52) U.S. Cl.
CPC .................................. *A61C 8/0001* (2013.01)
(58) Field of Classification Search
CPC ...... A61C 8/006; A61C 8/0066; A61C 8/0069; A61C 8/0089
USPC .............................. 433/62–214; 81/461, 483
See application file for complete search history.

(56) References Cited

U.S. PATENT DOCUMENTS

| 2,538,350 | A | * | 1/1951 | Baule | B25B 15/008 411/403 |
| 5,019,080 | A | * | 5/1991 | Hemer | A61B 17/8615 411/402 |
| 5,370,021 | A | * | 12/1994 | Shigematsu | B25B 15/008 81/436 |
| 6,131,493 | A | * | 10/2000 | Yamamoto | F16B 23/003 81/121.1 |
| 6,332,777 | B1 | * | 12/2001 | Sutter | 433/173 |
| 6,461,160 | B1 | * | 10/2002 | Sutter | A61C 8/0012 433/172 |
| 6,726,480 | B1 | * | 4/2004 | Sutter | A61C 8/0001 433/173 |
| 7,188,554 | B2 | * | 3/2007 | Baynham | F16B 23/003 411/402 |
| 8,953,984 | B2 | * | 2/2015 | Iijima | G03G 21/1671 399/167 |
| 2006/0278049 | A1 | * | 12/2006 | Baynham | F16B 23/003 81/436 |
| 2009/0104583 | A1 | * | 4/2009 | Yau et al. | 433/213 |
| 2010/0196853 | A1 | | 8/2010 | Zipprich | |

(Continued)

FOREIGN PATENT DOCUMENTS

DE    296 20 299    3/1997
EP    2 005 915 A1    12/2008

(Continued)

*Primary Examiner* — Matthew Saunders
(74) *Attorney, Agent, or Firm* — Henry M. Feiereisen LLC (57) ABSTRACT

An insertion post for transferring onto a model a location and orientation of at least one implant introduced in a jaw of a patient includes an insert piece insertable in the implant and to realize a fixed rotative connection with an interface of an internal opening of the implant. An end piece is arranged adjacent to the insert piece and tapers towards an apical end of the implant while substantially maintaining an outer contour of the insert piece.

15 Claims, 4 Drawing Sheets

(56) References Cited

U.S. PATENT DOCUMENTS

| | | | |
|---|---|---|---|
| 2011/0236849 A1* | 9/2011 | Pogorelsky | 433/24 |
| 2012/0137842 A1* | 6/2012 | Guo | F16B 23/003 81/460 |
| 2012/0141951 A1* | 6/2012 | Bellanca | A61C 8/0001 433/72 |
| 2012/0164599 A1* | 6/2012 | Holmstrom | A61C 8/005 433/173 |
| 2012/0237899 A1 | 9/2012 | Holmstrom | |

FOREIGN PATENT DOCUMENTS

| | | | | |
|---|---|---|---|---|
| EP | 2 570 097 A1 | | 3/2013 | |
| FR | 2985419 A1 | * | 7/2013 | A61C 8/0057 |

* cited by examiner

FIG. 1

PRIOR ART

FIG. 2

PRIOR ART

INSERTION POST FOR TRANSFERRING LOCATION AND ORIENTATION OF AT LEAST ONE IMPLANT INTRODUCED IN THE JAW OF A PATIENT ONTO A MODEL, AND ASSOCIATED IMPRESSION POST

CROSS-REFERENCES TO RELATED APPLICATIONS

This application claims the priority of European Patent Application, Serial No. EP 13153477.8, filed Jan. 31, 2013, pursuant to 35 U.S.C. 119(a)-(d), the disclosure of which is incorporated herein by reference in its entirety as if fully set forth herein.

BACKGROUND OF THE INVENTION

The invention relates to an insertion post for transferring the location and orientation of at least one implant introduced in a jaw of a patient onto a model.

The following discussion of related art is provided to assist the reader in understanding the advantages of the invention, and is not to be construed as an admission that this related art is prior art to this invention.

Patients who lost one or several teeth have nowadays various options to replace a lost tooth with a tooth replacement or artificial tooth. In addition to bridges which involve a tooth replacement mounted for example between still existing teeth, there are implants for providing adequate dental restoration. The implant is screwed in the position of the missing tooth into the jaw of the patient and has an abutment which is inserted in the implant to support the artificial tooth in form of a crown. The artificial tooth is provided in many cases not only for reasons of aesthetic. Medical criteria also are oftentimes relevant. When teeth are missing, the jaw may shift or shrink, and bones may degrade during the course of time in the absence of suitable restoration. In addition, teeth in the opposite jaw have no longer a counterpart and may extract from the jaw, causing further tooth loss.

To model the tooth replacement, typically a crown, the tooth or mouth structure of the patient is transferred to a master model. The mouth structure includes hereby the contours of the still existing teeth and also the position or location and orientation of the implants mounted in the bone. The orientation is hereby realized by indexing which typically is implemented in the implant by a rotationally restrained interface, oftentimes as hexagon socket. The abutment includes further an insert piece which provides with the implant a connection which is restrained against rotation. When the abutment and the crown are fabricated, it can be ensured in this way that the crown, when inserted, is correctly oriented and as envisioned in the model fits in the still existing tooth structure of the patient.

For transfer of the location and orientation of the implant, application of the closed and open tray techniques is known. In either technique, the mouth structure is transferred onto a model with the aid of impression material and impression posts that are inserted in the corresponding implant. An impression post for the open tray technique normally has an insertion post and a fixation element formed as a screw for fastening the insertion post to the implant. In the open tray technique, the insertion posts remain in the impression material, when removing the impression tray from the mouth. For this purpose, the fixation elements are loosened before removal of the impression tray. This is made possible by providing in the impression tray holes through which the fixation elements can be guided for loosening the insertion posts from the implants.

The provision of an impression is especially difficult when several substantially angled or pairs of skewed, non parallel, implants are involved simultaneously. As a result of the inevitable undercut of the connection to the implant, a kind of interlocking of the implants with one another is encountered because of the viscosity of the impression material. Impression of a group of interlocked implants is possible only in opposition to the substantially elastic resistance of the impression material. In other words, during removal of the impression material from the mouth, the impression material is deformed in some areas. In practice, impression materials do not behave completely elastic, so that the deformation is not completely reversed. This may lead to a substantial rebound inaccuracy of the impression material, potentially causing inaccuracies of the impression. The resistance of the impression material and the undercut of the connections to the individual implants may also cause uncomfort for the patient because the impression tray can be detached from the jaw only with increased force application.

It would therefore be desirable and advantageous to address these problems and to obviate other prior art shortcomings.

SUMMARY OF THE INVENTION

According to one aspect of the present invention, an insertion post for transferring onto a model a location and orientation of at least one implant introduced in a jaw of a patient includes an insert piece configured for insertion in the implant and to realize a fixed rotative connection with an interface of an internal opening of the implant, and an end piece arranged adjacent to the insert piece and tapering towards an apical end of the implant while substantially maintaining an outer contour of the insert piece.

The invention is based on the recognition that the determination of the orientation and location of the implant has to be carried out as accurately as possible, when obtaining the impression, since later on faults of the abutment as a result of inaccurate information can be corrected with difficulties or not at all. Faults causing a false determination of location and orientation of the implant can occur on one hand during insertion of the insertion posts in the implant, when, for example, during tightening of the screw by which the insertion post is firmly secured to the implant, oral mucosa or gingiva gets pinched, and no definite indexing is provided during tightening of the screw, or also as a result of mutual tilting of implant and insertion post. On the other hand, these faults may also be encountered during detachment of the impression material.

In open tray technique, which involves a loosening of the fixation element before removal of the impression tray from the mouth so that the insertion post can remain in the impression material, inaccuracies can occur when several implants which are askew to one another are anchored in a patient's jaw so that insertion and withdrawal directions are skewed in pairs. When being removed, the impression material is inevitably stretched or deformed until all insertion posts have been loosened from the implant. An insertion post for use in the open tray technique should therefore be detachable without causing excessive deformation of the impression material. This, of course, cannot be attempted at the expense of functionality. Furthermore the insertion post should be of simple structure, in particular of one-piece construction, so that its removal does not complicate handling caused by possible stretching of the impression material.

As has been recognized, these demands on an insertion post can be satisfied when the end piece of the insertion post, i.e. the piece which is introduced first into the implant, tapers while maintaining the shape or outer contour of the insert piece. The term "outer contour" relates hereby to a two-dimensional shape which is realized by a section through the insert piece in a plane which is perpendicular to the longitudinal direction of the implant. As a result of this tapered configuration, a lateral clearance is quickly provided, when the insertion post is extracted from the implant, while the upper end of the insertion post is embedded in the impression material, so that extraction is facilitated. In addition, the end piece is centered automatically due to its design during insertion of the insertion post in the implant before taking the impression and guides the insertion post to a position with defined index.

The inventive concept is applicable to all embodiments, in which a fixed rotative connection is provided between implant and abutment or implant and insertion post for adjustment or fixation of a defined indexing, and in which a tapering end piece adjoins while substantially maintaining the contour of this connection region, so that the face of this contour decreases as the taper increases.

According to another advantageous feature of the present invention, the interface can be constructed as a polygon, such as square or hexagon, with a plurality of edges, with the insert piece being prismatic and shape-congruent to the interface, wherein the end piece has inwardly inclined prism faces which can have a prismatic tapering configuration, with a number of the prism faces corresponding to a number of the edges of the polygon.

The flat surfaces between the prism edges thereby resemble certain trapezes. Such a configuration of the end piece is especially advantageous for the removal of the impression tray when several implants which are skewed in relation to one another are involved. When during loosening of the fixation element the insertion post is withdrawn from the implant and the insert piece has left the opening region of the implant, the insertion post can be significantly tilted relative to the implant in a direction of one of the edges of the opening region, without losing the indexing.

The farther the end piece is withdrawn from the implant, the more the insertion post can be angled. When a plurality of angled implants is involved, a best possible common direction can be realized in which the impression tray can be withdrawn, without great forces acting on the insertion post and the impression material. Thus, an especially accurate impression can be produced. During removal, orientation or indexing is maintained so that the risk of inaccuracies is avoided. A tilting of the insertion post relative to the implant during removal can be executed in six different directions associated with the edges of the opening region of the implant. This provides sufficient possibilities to withdraw from the implant insertion posts which are angled to one another, without significantly deforming the impression material.

The terms "prism" or "prismatic" are used within the scope of the invention in a geometric sense for a body with a polygonal base surface which is displaced parallel. A prismatic taper relates here to a prism having a circumference around the corners which decreases in a plane parallel to its base surface in a direction perpendicular to the base surface.

According to another advantageous feature of the present invention, an angle between a longitudinal direction of the implant and a respective one of the prism faces can range from 7.5° to 20°. Currently preferred is an angle of 15°. Angles having these values enable the option to quickly tilt the insertion post and prevent an excessive narrowing of the cross section of the end piece that would cause a relatively rapid loss of the fixed rotative connection with the implant.

According to another advantageous feature of the present invention, the interface can be constructed as a polygonal socket with inner rounded sides and the insert piece can be constructed as an polygonal socket with outer rounded sides in shape-congruent relationship to the polygon socket of the interface, with the end piece being constructed as a tapering polygonal socket with outer rounded sides.

According to another advantageous feature of the present invention, the insert piece has in a longitudinal direction of the implant an extension which can be significantly smaller than an extension of the end piece. Currently preferred is an extension of the insert piece in the longitudinal direction of the implant which is more than twice as small than the extension of the end piece. In other words, the length of the end piece is advantageously twice as long as the length of the insert piece, as seen in the longitudinal direction of the implant. This has the following benefit: as the insertion post is withdrawn from the implant, tilting of the insertion post relative to the implant is not possible only over a short distance, during which the end piece is still located at least partially in the opening region of the implant. For a significantly longer piece, while still being restrained against rotation, the insertion post can be tilted.

According to another advantageous feature of the present invention, the end piece can have in a longitudinal direction of the implant an extension which is between 0.5 mm and 1.5 mm. Currently preferred is an extension of the end piece in the longitudinal direction of the implant of 0.8 mm. This is especially advantageous when the angle is in the above mentioned ranges.

According to another advantageous feature of the present invention, the insert piece can have in a longitudinal direction of the implant an extension which is between 0.2 mm and 1.0 mm. In this way, tilting of the insertion post is possible after withdrawal of the insertion post over a shortest possible distance. Currently preferred is an extension of the insert piece in the longitudinal direction of the implant of 0.4 mm.

According to another advantageous feature of the present invention, the extension of the insert piece and/or the extension of the end piece in the longitudinal direction of the implant can be significantly smaller than the length of the implant and/or the length of the insertion post. In other words, the longitudinal dimensioning of the insert piece and the end piece is selected of a size sufficient to realize the desired functionality during withdrawal of the impression tray.

According to another aspect of the present invention, an impression post includes an insertion post for transferring onto a model a location and orientation of at least one implant introduced in a jaw of a patient, with the insertion post comprising an insert piece configured for insertion in the implant and to realize a fixed rotative connection with an interface of an internal opening of the implant, and an end piece arranged adjacent to the insert piece and tapering towards an apical end of the implant while substantially maintaining an outer contour of the insert piece, and a fixation element configured to secure the insertion post to the implant.

According to another advantageous feature of the present invention, the fixation element can be a screw.

The present invention has many advantages as a result of the provision of a tapering end piece because stretching and deformation of the impression material can be significantly avoided, even in the presence of a plurality of implants that are askew in relation to one another, so that the realization of a very precise impression is made possible. Also during insertion, which involves introduction of the insertion post into the implant before impression taking, the configuration of the end piece provides benefits because due to the tapering configuration there is no need for a precise guidance of the insertion post from above or parallel to the implant. Also during insertion of the insertion post in the implant, the dentist gains substantially more confidence and comfort, because the insert piece due to its special shape virtually automatically centers in the inner opening region of the implant and automatically has a secure index in the end position.

A prismatically designed taper provides substantial clearance space for tilting the insertion post relative to the implant, and the indexing can be maintained at the same time during withdrawal of the insertion post from the implant.

An impression post with such an insertion post enables a precise implementation of the impression process.

BRIEF DESCRIPTION OF THE DRAWING

Other features and advantages of the present invention will be more readily apparent upon reading the following description of currently preferred exemplified embodiments of the invention with reference to the accompanying drawing, in which.

DETAILED DESCRIPTION OF PREFERRED EMBODIMENTS

Throughout all the figures, same or corresponding elements may generally be indicated by same reference numerals. These depicted embodiments are to be understood as illustrative of the invention and not as limiting in any way. It should also be understood that the figures are not necessarily to scale and that the embodiments are sometimes illustrated by graphic symbols, phantom lines, diagrammatic representations and fragmentary views. In certain instances, details which are not necessary for an understanding of the present invention or which render other details difficult to perceive may have been omitted.

Figure 1:
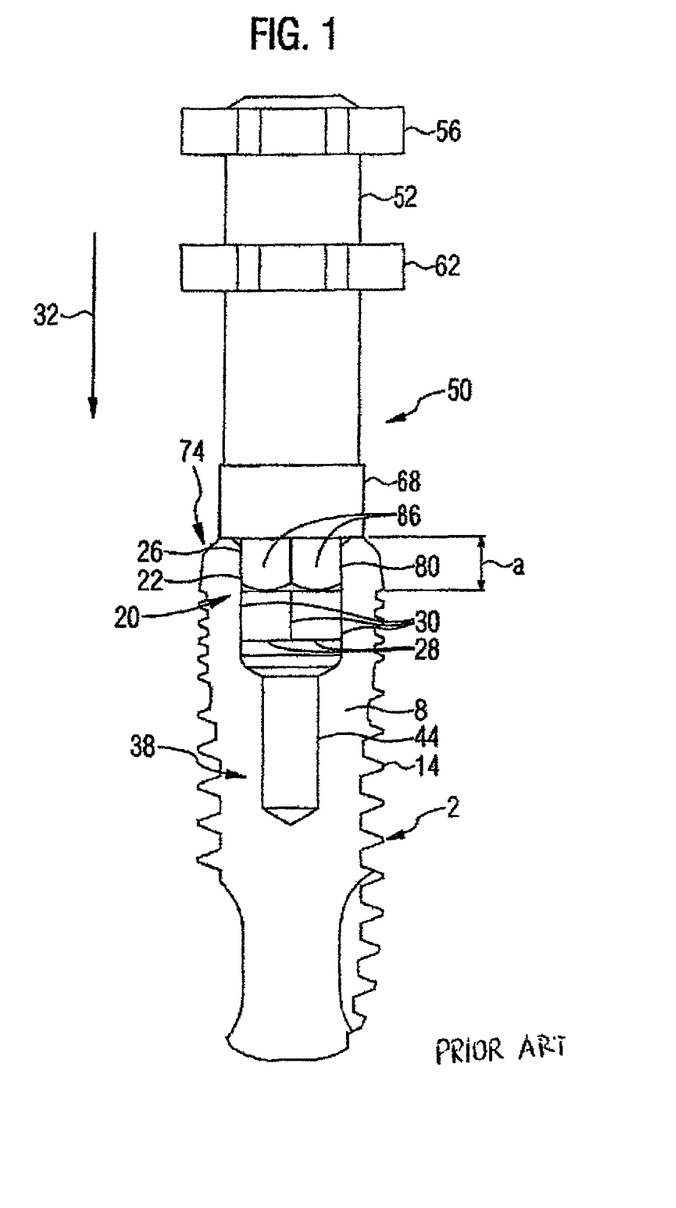
FIG. 1 is a lateral cross section of a tooth implant with a first variation of an inserted insertion post according to the prior art.

Turning now to the drawing, and in particular to FIG. 1, there is shown a lateral cross section of a tooth implant SICmax 2 as known from the prior art and including an implant body 8 with an outer thread 14 for screwing in the patient's jaw. A multi-edge opening region 20 with an interface 22 is provided on an end of the implant 2 in facing relationship to the cavity of the patient's mouth. The interface 22 includes an hexagon socket 26 with six edges 28 to form a hexagon, and six longitudinal edges 30. As seen in the longitudinal direction 32 of the implant, a substantially cylindrical inner region 38 with an inner thread 44 adjoins the opening region 20. A fixation element, in particular a screw, can be threadably engaged into the inner thread 44 to form an abutment with the implant 2.

A conventional insertion post 50 with a post body 52 is inserted in the implant 2. The insertion post 50 is provided to transfer the position and orientation of the implant 2 when taking an impression of the jaw, using the open tray technique, in which the insertion post 50 remains in the impression material, when the impression tray is removed from the patient's mouth. Before taking the impression, the insertion post 50 is connected with the implant 2 by a screw which is screwed in the inner thread 44. The post body 52 of the insertion post 50 has an upper collar 56 and a lower collar 62. The collars 56, 62 serve as retention elements for preventing horizontal, vertical and rotational displacements during removal of the impression tray from the mouth. The post body 52 has moreover an attachment 68 which bears upon an edge 74 of the implant body 8, when threadably connected to the post body 52.

To realize a fixed rotative engagement with the implant 2, the insertion post 50 has an insert piece 80 which has a prismatic shape and is formed as an outer hexagon socket with six hexagonal faces 86. The insert piece 80 has a length of 1.2 mm and thus extends in the longitudinal direction 32 in the opening region 20 only up to midsection thereof.

When taking an impression of several implants 2 which are askew relative to one another, deformations and stresses are caused in the impression material during removal of the impression material as the insertion posts 50 are withdrawn in opposition to the longitudinal direction 32 until the respective insert piece 80 has left the opening region 20. As the length a of the insert piece 80 is 1.2 mm, the insertion posts 50 have to be withdrawn also exactly over the distance of 1.2 mm. As a consequence of the resultant stretching of the impression material, the replication of the implant positions and implant orientations becomes inaccurate. This can lead to the situation that the tooth replacement modeled with the aid of the model does not fit or fits only poorly at the desired place. Corrections, if at all possible, are difficult and cost intensive.

Figure 2:
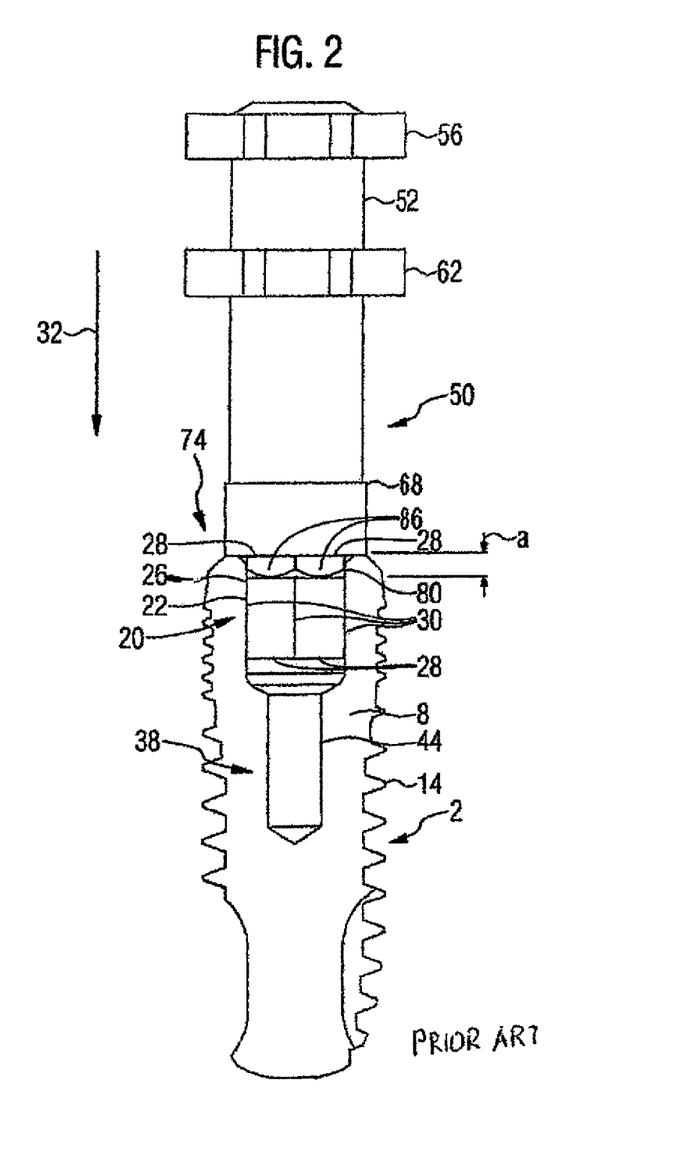
FIG. 2 is a lateral cross section of a tooth implant with a second variation of an inserted insertion post according to the prior art.

FIG. 2 shows a lateral cross section of a tooth implant with a second variation of an inserted insertion post 50 which differs from the insertion post of FIG. 1 by the smaller length a of the insert piece 80 which length a is 0.4 mm. Thus, provision is made for a spatial clearance sooner as the insertion post 50 is extracted from the implant 2 in an attempt to lessen the risk of stretching of the impression material. Even if stretching of the impression material is less, there is still the drawback that orientation or indexing and thus corresponding guidance get lost also much sooner. In addition, also insertion of the insertion post 50 in the implant has little guidance, rendering this procedure more difficult and uncomfortable for a dentist. Furthermore, the insertion post 50 of FIG. 2 has the disadvantage that tissue residues (oral mucosa or bone edges) can prevent insertion of the short insert piece in the orientation or indexing.

Figure 3:
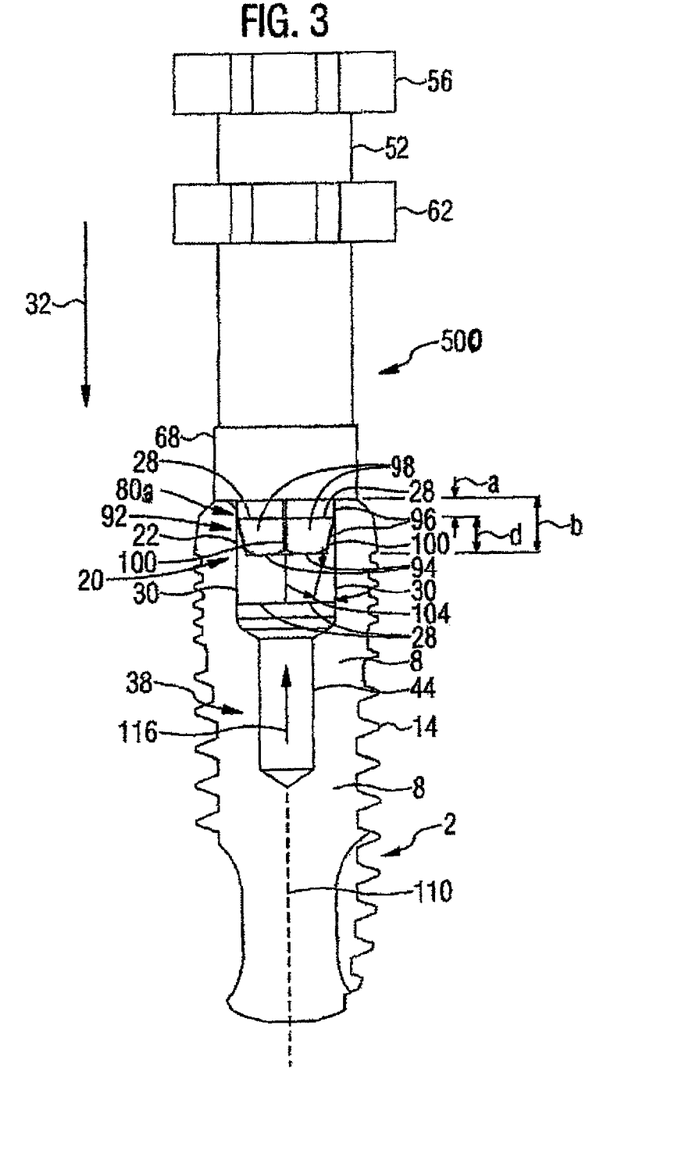
FIG. 3 is a lateral cross section of a tooth implant with inserted insertion post in accordance with the present invention.

Referring now to FIG. 3, there is shown a lateral cross section of a tooth implant with inserted insertion post in accordance with the present invention, generally designated by reference numeral 500. In the following description, parts corresponding with those in FIGS. 1 and 2 will be identified, where appropriate for the understanding of the invention, by corresponding reference numerals followed by an "a". The insertion post 500 has an insert piece 80a with a length a of 0.4 mm and an end piece 92 with an outer contour 96 adjacent to the insert piece 80a in longitudinal direction 32 or apical direction of the implant. The outer contour 96 continuously tapers in the longitudinal direction 32. The end piece 92 is configured as a prism with tapering outer contour to resemble a truncated pyramid which is generalized with respect to the number of its corners. In other words, instead of four corners and edges, the end piece 92 has six corners and edges. The end piece 92 has six prism faces 98, which are bounded on one side by the edges 28 and on an opposite side by inner edges 94. The end piece 92 represents a tapered pin essentially for insertion in the opening region 20 of the implant and smoothly adjoins the insert piece 80a.

The provision of the insertion post 500 according to the present invention substantially eliminates the afore-described problems of conventional insertion posts, when impression material is removed and a plurality of implants is involved which are skewed relative to one another. As a result of the prismatically tapering end piece 92, a suitable tilting of the respective insertion post 500 relative to the implant 2 enables the realization of a common or coincidental direction in which the insertion posts 500 can be extracted from the associated implants 2. In other words, the insertion posts 500 are substantially oriented parallel to one another. At the same time, the presence of a fixed rotative engagement and formfitting connection between insertion post 500 and opening region 20 of the implant 2 are maintained so that during tilting of the respective insertion post 500, the latter is prevented from easily turning and causing the impression material to stretch or deform that would result in inaccuracies of the impression taking.

A length b which includes the length a, i.e. the extension of the insert piece 80a in the longitudinal direction 32 of the implant, and the extension of the end piece 92, is 1.3 mm long in this non-limiting example, so that a length d is established for the end piece 92 of 0.8 mm. The end piece 92 is thus sized more than twice the length of the end piece 80. Thus, a fixed rotative connection can be maintained over the length d, while the insertion post 500 can be tilted in relation to the longitudinal direction 32. A rigid fixed rotative engagement is maintained as long as the insert piece 80a is received inside the opening region 20.

An angle c between the longitudinal direction 32 and a direction 104 which designates the inclination of the respective prism face 98 inwardly in relation to a central axis 110 of the implant, is 15° in the present non-limiting example. This ensures that the fixed rotative engagement is maintained substantially over the entire length of the end piece 92.

Figure 4:
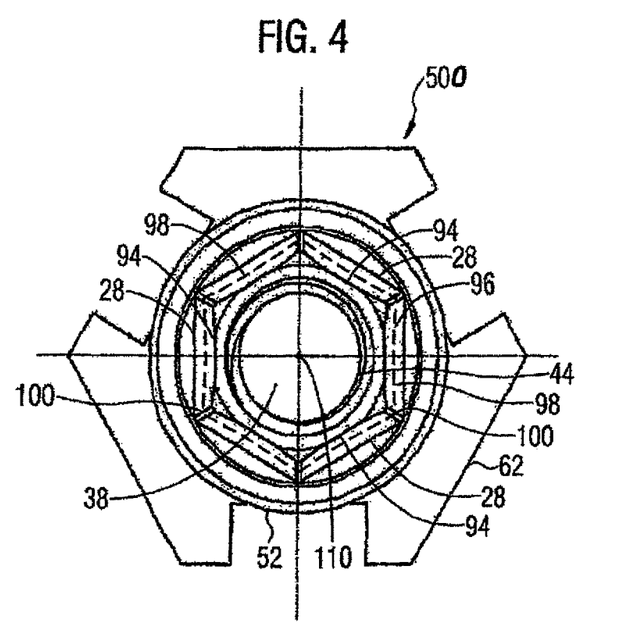
FIG. 4 is a bottom view of the insertion post of FIG. 3.

FIG. 4 shows the insertion post 500 from a direction 116 indicated in FIG. 3. The prism faces 98 are each bounded by the edges 28, the inner edges 94 and the intermediate edges 100 between the prism faces 98. The prism faces 98 respectively extend with their inner edges 94 only so far radially in the direction 110 that the inner region 38 is still accessible for the screw or the fixation element. The end piece 92 tapers between the edges 28 and the inner edges 94 while maintaining its outer contour 96.

While the invention has been illustrated and described in connection with currently preferred embodiments shown and described in detail, it is not intended to be limited to the details shown since various modifications and structural changes may be made without departing in any way from the spirit and scope of the present invention. The embodiments were chosen and described in order to explain the principles of the invention and practical application to thereby enable a person skilled in the art to best utilize the invention and various embodiments with various modifications as are suited to the particular use contemplated.

What is claimed as new and desired to be protected by Letters Patent is set forth in the appended claims and includes equivalents of the elements recited therein:

What is claimed is:

1. A combination, comprising:
   at least one implant having an internal opening extending in a longitudinal direction;
   an insertion post configured to transfer onto a model a location and orientation of a single implant and a plurality of angled implants introduced in a jaw of a patient, said insertion post comprising a post body and a post part extending from the post body, insertable in the internal opening of the implant and consisting of a single insert piece insertable in the longitudinal direction in fixed rotative connection in the internal opening of the implant, and a single end piece arranged adjacent to the insert piece, said insert piece having a constant cross section over its whole extent in the longitudinal direction corresponding to a transverse cross section of the internal opening of the implant, while said single end piece tapering away from said insert piece in the longitudinal direction towards an apical end of the implant while fully maintaining an outer contour of the insert piece over a whole extent of the end piece in the longitudinal direction, said end piece being formed as a tapered pin and smoothly adjoining the insert piece, said end piece having an insert-piece-proximal end defined by a cross section which is greater than a cross section at an insert-piece-distal end of the end piece, and
   an interface constructed as a polygon with a plurality of edges, with the insert piece being prismatic and shape-congruent to the interface,
   wherein the end piece has inwardly inclined prism faces which have a prismatic tapering configuration with a number of the prism faces corresponding to a number of the edges of the polygon.

2. The combination of claim 1, wherein the insert piece is prismatic and shape-congruent to the internal opening of the implant, said end piece having inwardly inclined prism faces which have a prismatic tapering configuration, with a number of the prism faces corresponding to a number of the edges of the polygon.

3. The combination of claim 2, wherein the prism faces are inclined at an angle in a range of 7.5° to 20° in relation to a central axis of the insertion post.

4. The combination of claim 3, wherein the angle is 15°.

5. The combination of claim 1, the insert piece is polygonal and has outer rounded sides in shape-congruent relationship to the opening region of the implant, said end piece being constructed as a tapering polygonal socket with outer rounded sides.

6. The combination of claim 1, wherein the insert piece has an extension which is smaller than an extension of the end piece.

7. The combination of claim 6, wherein the extension of the insert piece is more than twice as small than the extension of the end piece.

8. The combination of claim 1, wherein the end piece has an extension which is between 0.5 mm and 1.5 mm.

9. The combination of claim 8, wherein the extension of the end piece is 0.8 mm.

10. The combination of claim 1, wherein the insert piece has in a longitudinal direction of the implant an extension which is between 0.2 mm and 1.0 mm.

11. The combination of claim 10, wherein the extension of the insert piece is 0.4 mm.

12. A combination, comprising:

at least one implant having an internal opening extending in a longitudinal direction;

an impression post, comprising an insertion post configured to transfer onto a model a location and orientation of a single implant and a plurality of angled implants introduced in a jaw of a patient, said insertion post comprising a post body and a post part extending from the post body, insertable in the internal opening of the implant and consisting of a single insert piece insertable in the longitudinal direction in fixed rotative connection in the internal opening of the implant, and a single end piece arranged adjacent to the insert piece, said insert piece having a constant transverse cross section over its whole extent in the longitudinal direction corresponding to a transverse cross section of the internal opening of the implant, while said single end piece tapering away from said insert piece in the longitudinal direction towards an apical end of the implant while fully maintaining an outer contour of the insert piece over a whole extent of the end piece in the longitudinal direction, said end piece being formed as a tapered pin inserted in the opening region of the implant and smoothly adjoining the insert piece of the insertion post piece, said end piece having an insert-piece-proximal end defined by a cross section which is greater than a cross section at an insert-piece distal of the end piece, and an interface constructed as a polygon with a plurality of edges, with the insert piece being prismatic and shape-congruent to the interface, wherein the end piece has inwardly inclined prism faces which have a prismatic tapering configuration with a number of the prism faces corresponding to a number of the edges of the polygon; and a fixation element securing the insertion post to the implant.

13. The combination of claim 12, wherein the fixation element is a screw.

14. The combination of claim 1, wherein said end piece of the insertion post has a plurality of radially inner edges which are arranged after one another in a circumferential direction and have a radially inwardly concave rounded shape.

15. The combination of claim 12, wherein said end piece of the insertion post has a plurality of radially inner edges which are arranged after one another in a circumferential direction and have a radially inwardly concave rounded shape.

* * * * *